Aug. 27, 1974 L. B. SHERRILL Plant Pat. 3,603
PEACH TREE
Filed July 12, 1973
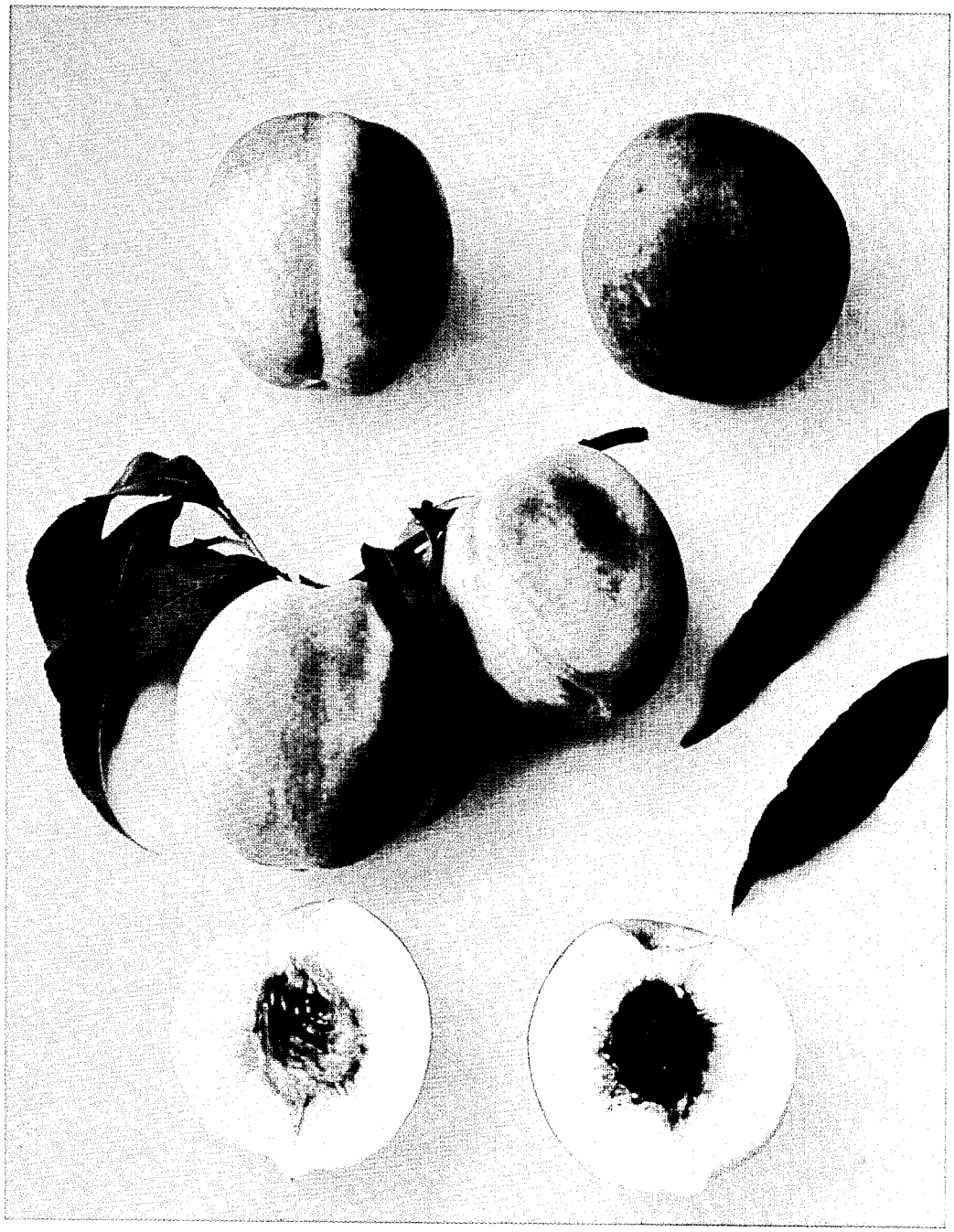

United States Patent Office

Plant Pat. 3,603
Patented Aug. 27, 1974

3,603
PEACH TREE

Lewis B. Sherrill, Rte. 2, Box 536,
Bakersfield, Calif. 93307

Filed July 12, 1973, Ser. No. 378,781
Int. Cl. A01h 5/03
U.S. Cl. Plt.—43 1 Claim

ABSTRACT OF THE DISCLOSURE

A peach tree of medium size, medium vigor, spreading growth, vase-form, hardy for California peach producing areas, abundantly foliated with large, uniform, lanceolate, deep-green leaves having a crenate margin and reniform glands, medium in blooming period with light pink showy flowers, and a regular and productive bearer of large, uniform, globose, freestone fruit having yellow skin substantially overspread with red, yellow flesh, and a red pit cavity with the red streaked into the flesh.

Origin of the variety: The present variety of peach tree was discovered by me on a fruit-bearing branch which occurred as a mutation on a Fairtime (unpatented) peach tree in the secondary scaffold of such tree. The peach tree upon which the mutation occurred was growing in an orchard on a ranch in Kern County, Calif., and which orchard was under my supervision. I recognized that the fruit borne by the mutation limb had characteristics which were new and distinct, and I, therefore, undertook asexual reproduction of the variety.

Asexual reproduction of the variety: I asexually reproduced the present variety of peach tree by removing scion buds from the mutation limb, and implanting such scion buds in a number of existing peach trees within the same orchard where the mutation occurred. Such asexual reproductions—upon bearing fruit—ran true in all respects to the original discovery; i.e., the parent mutation limb and the fruit borne thereby. No evidence is present of incompatibility of any graft unions in the reproduction of the present variety of peach tree.

Summary of the variety: The herein claimed variety of peach tree is of medium size, medium vigor, spreading growth, vase-form, hardy for California peach producing areas, abundantly foliated with large, uniform, lanceolate, deep-green leaves having a crenate margin and reniform glands, medium in blooming period with light pink showy flowers, and a regular and productive bearer of large, uniform, globose, freestone fruit having yellow skin substantially overspread with red, yellow flesh, and a red pit cavity with the red streaked into the flesh; the variety being particularly characterized, in comparison with the Fairtime peach (an unpatented introduction of the Department of Agriculture, Fresno, Calif., station), by substantial likeness in its excellent qualities in tree productiveness, and fruit size, appearance, skin color including good blush color at the apex, flesh color, and flavor, but distinct—as to novelty—by fruit which ripens about thirty days earlier, and has a light yellow suture line.

The present variety of peach tree is further distinctively characterized, in comparison with the Summerset peach (an unpatented introduction of the Department of Agriculture, Fresno, Calif., station) by ripening fifteen to twenty days earlier.

Brief description of the drawing: The drawing is an illustration, by photographic reproduction in color, of a twig with leaves and attached fruit, detached leaves, and detached fruit; one of the latter being cut in half to expose the flesh, with the stone remaining in place in one of the cut halves.

Description of the variety: The botanical details of this new and distinct variety of peach tree—with color definitions (except those in common color terms) referenced to Maerz and Paul Dictionary of Color—are as follows:

Tree
- *Size.*—Medium.
- *Vigor.*—Medium.
- *Growth.*—Spreading.
- *Form.*—Vase.
- *Hardiness.*—Hardy for California peach growing areas.
- *Production.*—Excellent.
- *Bearing.*—Regular.

Trunk
- *Size.*—Medium.
- *Texture.*—Medium.

Branches
- *Size.*—Medium.
- *Texture.*—Medium.
- *Color.*—Brown.
- *Surface.*—Dull.
- *Lenticles.*—Number: Few. Size: Medium to small. Position: Not uniform.

Leaves
- *Size (Mature).*—Large. Average length—7⅝". Average width—1⅝".
- *Form.*—Lanceolate. Uniform.
- *Abundance.*—Abundant.
- *Thickness.*—Medium.
- *Texture.*—Smooth. No pubescence on underside of leaf.
- *Margin.*—Evenly crenate.
- *Petiole.*—Medium size. Average length—½".
- *Glands.*—Reniform. Medium to large. Opposite. Pale yellow.
- *Stipules.*—None.
- *Color.*—Top side—Deep green (23–L–8). Under side—Lighter green (22–K–6).

Flower buds
- *Hardiness.*—Hardy for California peach production. Dormancy requirements is 750 hours chilling below 45 degrees F.
- *Form.*—Plump. Pointed at apex.
- *Color.*—Light pink.

Flowers
- *Blooming Period.*—First bloom about March 2nd, coinciding with most commercial peach bloom.
- *Color.*—Showy, Light pink. Petals open flat showing a deeper pink at the base of each petal.

Fruit
- *Maturity When Described.*—Firm ripe.
- *Average Date Of First Picking.*—August 8th.
- *Average date Of Last Picking.*—August 17th.
- *Size.*—Large. Average diameter axially—3"–3⅛". Average transversely in suture plane—3"–3⅛".
- *Form.*—Globose, with a very small point at the blossom end. Uniform over the entire tree.
- *Suture.*—Distinct. Extends from base to apex. Slightly depressed. Light yellow.
- *Ventral Surface.*—Uniformly rounded.
- *Cavity.*—Uniformly rounded.
- *Base.*—Rounded.
- *Apex.*—Round, with a slight depression opposite the suture line.
- *Pistil Point.*—Slightly pointed.

Skin
- *Tendency To Crack.*—None.
- *Color.*—Deep yellow (11–L–5), substantially overspread with red (5–J–6) shading to darker red (7–E–6), with very few mottled areas; the red overspreading 60 to 80 percent of the skin. The stem cavity is primarily yellow.

Flesh
- *Amygdalin.*—None.
- *Juice.*—Moderate.

*Texture.*—Medium to firm.

*Fibers.*—Moderate and very fine. Extend from the pit and are not pronounced. Light in color.

*Ripens.*—Uniformly, including the stem cavity.

*Flavor.*—Sub-acid. Distinct.

*Aroma.*—Distinct. Desirable.

*Eating Quality.*—The flash qualities in firmness and flavor are excellent.

*Color.*—Deep yellow (10–L–4).

*Surface Of Pit Cavity.*—Red (5–L–6), with the red streaked into the flesh.

Stone

*Type.*—Freestone. Breaks free from flesh at firm-ripe maturity.

*Size.*—Medium. Average length—1⅛". Average breadth—⅞". Average thickness—⅝".

*Form.*—Oblong. Sharply pointed at pistil point. Irregularly cuneate at apex.

*Hilum.*—Oblong. Narrowly indented.

*Apex.*—Acuminate. Very sharp at point.

*Sides.*—Unequal.

*Surface.*—Irregularly furrowed and pitted.

*Ridges.*—Interrupted, both sides.

*Ventral Edge.*—Thin. Irregular. Fading at apex.

*Dorsal Edge.*—Pronounced. Unevenly cuneate near apex.

*Tendency To Split.*—None.

*Fertility.*—Self-fertile.

*Color.*—Dark brown (8–L–10).

Use

Fresh table dessert. Freestone canning. Freezing.

Keeping quality

Fruit matures uniformly and maintains good firmness for normal handling and processing for its markets.

Resistance to disease

Equal to other commercial peach varieties.

The tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, characterized by substantial similarity in tree productiveness, and freestone fruit size, appearance, skin color, flesh color, and flavor to the Fairtime peach, but distinct—as to essential novelty—by fruit which ripens about thirty days earlier; and further characterized, in comparison to the Summerset peach, by ripening fifteen to twenty days earlier.

No references cited.

ROBERT E. BAGWILL, Primary Examiner